United States Patent
Ichida et al.

(10) Patent No.: US 6,189,368 B1
(45) Date of Patent: Feb. 20, 2001

(54) METHOD AND APPARATUS FOR DETECTION OF CONCENTRATION OF HYDROGEN PEROXIDE VAPOR

(75) Inventors: Taizo Ichida, Ibaraki-ken; Shinichi Ando; Akihide Terao, both of Saitama-ken, all of (JP)

(73) Assignee: Taiyo Toyo Sanso Co., Ltd., Osaka (JP)

(*) Notice: Under 35 U.S.C. 154(b), the term of this patent shall be extended for 0 days.

(21) Appl. No.: 09/198,576

(22) Filed: Nov. 24, 1998

(30) Foreign Application Priority Data

Nov. 28, 1997 (JP) .................................... 9-327266

(51) Int. Cl.[7] .................................................. G01N 27/12
(52) U.S. Cl. ................................... 73/31.06; 422/88
(58) Field of Search .......................... 73/31.06; 422/83, 422/88

(56) References Cited

U.S. PATENT DOCUMENTS 5,608,156 * 3/1997 Ando et al. ......................... 73/31.06
5,882,590 * 3/1999 Stewart et al. ....................... 422/28

FOREIGN PATENT DOCUMENTS

1425685 * 2/1976 (GB) ..................................... 73/31.05
2165948 * 4/1986 (GB) ..................................... 73/31.06
8-271464 * 10/1996 (JP) ..................................... 73/31.06

* cited by examiner

Primary Examiner—Daniel S. Larkin
(74) Attorney, Agent, or Firm—Griffin & Szipl, PC

(57) ABSTRACT

Real-time and accurate detection of the concentration of hydrogen peroxide vapor supplied into a treatment vessel is made possible by a method and apparatus that permits efficient and effective sterilization, disinfection, or the like with hydrogen peroxide vapor. The concentration of hydrogen peroxide vapor in a treatment vessel is detected by a semiconductor gas sensor in a treatment system where an object to be treated is brought into contact with hydrogen peroxide vapor in a treatment vessel with the pressure fixed at a constant level. The output of the semiconductor gas sensor is revised by an arithmetic unit in relation to the temperature and/or the humidity in the treatment vessel detected on the basis of data, worked out in advance, representing the correlation between the output of the semiconductor gas sensor and the concentration of hydrogen peroxide vapor in which the temperature and/or the humidity are parameters, and the value thus revised is indicated on a concentration indicator as concentration of hydrogen peroxide.

4 Claims, 10 Drawing Sheets

METHOD AND APPARATUS FOR DETECTION OF CONCENTRATION OF HYDROGEN PEROXIDE VAPOR

BACKGROUND OF THE INVENTION

1. Field of the Invention

The present invention relates to detection of a concentration of hydrogen peroxide vapor in a treatment vessel, and more particularly to a method and apparatus for detection of the concentration of hydrogen peroxide vapor by means of a semiconductor gas sensor, in a system for such treatments as sterilization and disinfection, by bringing an object for treatment into contact with hydrogen peroxide vapor in a treatment vessel, with at least the pressure kept at a constant level.

2. Description of the Prior Art

Since hydrogen peroxide vapor decomposes itself into harmless oxygen and water when coming into contact with a solid and generates nascent oxygen with sterilization and other effects, it can be used as a sterilizing agent and disinfectant and offers a wide range of application possibilities. It is currently used in sterilizing and disinfection treatments of such objects as pharmaceutical basic materials, pharmaceutical end products, and food packaging, in the pharmaceutical, medical supply and equipment manufacturing, and food industries. In such treatments, hydrogen peroxide vapor in a specific concentration is supplied under a certain pressure, generally under atmospheric pressure, into a treatment vessel storing therein objects to be treated, for example, packaging materials placed therein, to sterilize and disinfect those objects by bring them into contact with hydrogen peroxide vapor.

The problem is, however, that the concentration of hydrogen peroxide vapor drops with time in the treatment vessel because it is decomposed and consumed when the vapor is in contact with the object to be treated and the inner wall of the vessel itself. Sterilization and disinfection with hydrogen peroxide utilizes nascent oxygen which is generated from a decomposition of hydrogen peroxide. Sterilization and disinfection thus becomes ineffective when the concentration of hydrogen peroxide vapor falls below a certain level. Yet, it would be quite wasteful to supply too much hydrogen peroxide vapor into the vessel and keep the concentration higher than necessary for sterilization and disinfection. In addition, disposal of excess hydrogen peroxide vapor would add a cost burden, because it would be necessary to enlarge facilities for treating the excess vapor before releasing it into the atmosphere.

To perform sterilization and disinfection efficiently, the concentration of hydrogen peroxide vapor in a treatment vessel has to be controlled and maintained in a proper range. If such concentration control is to be exercised properly, it is essential to detect precisely and in real time the concentration of hydrogen peroxide in the vessel.

Among the known methods of directly detecting the concentration of hydrogen peroxide are the controlled potential electrolysis, test-paper photoelectric photometry, and detection tube methods. None of these allows real-time detection of the concentration of hydrogen peroxide vapor, however. Accordingly, none of these is suitable for detection of the concentration of hydrogen peroxide vapor in such treatments as sterilization and disinfection.

The controlled potential electrolysis method uses a concentration detector comprising a working electrode and a counter electrode arranged in a region for containing the electrolytic solution, isolated from the outside by a partition. As the hydrogen peroxide vapor penetrates the partition and diffuses into the region for containing the electrolytic solution, it is adsorbed on the working electrode comprising an electrochemical catalyst, and causes an oxidation or reduction reaction to generate electric current between the electrodes, which is measured, thereby detecting the concentration of hydrogen peroxide vapor. The problem with this method is that the hydrogen peroxide vapor, that is, the gas to be detected which has diffused into the electrolytic solution-containing region, will be adsorbed by and remain in the electrolytic solution after detection is over (i.e., after the sterilization operation is completed with the hydrogen peroxide vapor removed from within the treatment vessel) and the hydrogen peroxide by the working electrode will not be removed for a long time. That is especially the case where the concentration of hydrogen peroxide vapor applied is high enough for effective sterilization and disinfection, not lower than 500 ppm, for example. The use of the vapor in very low concentrations, 10 ppm, for example, does not present this problem. With the working electrode in such condition, the concentration detector is very low in sensitivity to the change in the concentration of hydrogen peroxide and cannot determine the concentration of hydrogen peroxide in real time and accurately.

The test-paper photoelectric photometry method is carried out by a concentration detector with test paper incorporated therein, the test paper which is given a special treatment with a chemical so as to color upon contact with the hydrogen peroxide vapor. By measuring the intensity of the coloring of the test-paper, the concentration of hydrogen peroxide vapor is detected. The test paper contains, in addition to the coloring chemical, a certain amount of water to facilitate the coloring. The trouble is that when it comes into contact with the moisture contained in the test paper, the hydrogen peroxide vapor is dissolved in the water, resulting in a changed concentration of hydrogen peroxide vapor around the concentration detector, which makes accurate detection virtually impossible. Meanwhile, the object to be treated is often put into the treatment vessel and dried, because if moisture is on the object to be treated in sterilization and disinfection, the hydrogen peroxide vapor is dissolved, thereby reducing the effectiveness of hydrogen peroxide vapor sterilization of the object to be treated. But if the object is dried in the vessel, the test paper in the concentration detector mounted therein will be dried as well and the moisture contained in the test paper evaporates out of the test paper. Thus, accurate detection of the hydrogen peroxide vapor is virtually impossible with such test paper. Furthermore, there is a concern that the chemical contained in the test paper can stain the object to be treated when it evaporates. As pointed out, the test paper photoelectric photometry method is not suited and can not be adopted as method for detection of the concentration of hydrogen peroxide vapor in sterilizations and disinfections that have to be performed in a low-humidity atmosphere.

The detection tube method utilizes a concentration detector with a glass tube filled with a detector agent which undergoes a chemical reaction and changes in color on contact with hydrogen peroxide vapor in the tube. The idea is that as the hydrogen peroxide vapor is led into the glass tube through the mouth of the tube, the detector agent changes in color. The length of the color change is measured by a scale on the glass tube to determine the concentration of hydrogen peroxide vapor. But this method does not permit continuous detection of concentration and can not determine the concentration of hydrogen peroxide vapor real-time.

Having determined that the semiconductor sensor widely used for the detection of the concentration of $H_2$, CO, alcohol, and other chemicals could be applied to detection of hydrogen peroxide vapor, the present inventors have developed a method for detection of hydrogen peroxide (this shall be called prior art in the present specification) comprising providing a semiconductor gas sensor inside a treatment vessel with a concentration indicator outside, so that the output of the semiconductor gas sensor was converted into the concentration of hydrogen peroxide vapor and the measurement was indicated on the concentration indicator.

The aforesaid semiconductor gas sensor generally comprises a sensor element made of sintered metal oxide, electrodes embedded therein, and a means for heating the sensor element (indirect or direct heating type). The principle of this prior art method is this: when the gas constituents are adsorbed on the surface of such oxide particles as n-type semiconductor oxide and p-type semiconductor oxide, the free electrons around the surface move to change the electro-conductivity. This change in electro-conductivity is detected. If the hydrogen peroxide is chemically adsorbed by the oxide semiconductor element in the treatment vessel, the free electrons move in the element, increasing the electro-conductivity of the element. This reaction takes place in a very short time. That is, the sensor output quickly reflects the change in concentration.

Meanwhile, the concentration indicator, to which the output signals are constantly input from the semiconductor gas sensor, indicates the hydrogen peroxide vapor concentration, a converted value of the output of the semiconductor gas sensor. The conversion rate is set beforehand on the basis of data from an experiment representing the relation between the sensor output and the concentration of the hydrogen peroxide vapor. The experiment is conducted in accordance with the following procedure: the aqueous solution of hydrogen peroxide having the same properties as the one to be used in sterilization and disinfection is injected by micro syringe into a closed experiment vessel (heat-resistant vessel) filled with a clean atmosphere and is completely evaporated by heating instantly by a heater or the like. With the temperature and humidity inside the experiment vessel maintained at constant level, measurements are taken of the output of the semiconductor gas sensor mounted in the experiment vessel. That is, the decrease in resistance is converted into the increase in voltage as in an electric circuit. The quantity of aqueous hydrogen peroxide injected is varied, and the outputs of the sensor are measured at different levels of the amounts as injected, and thus the relation between the output of the sensor and the concentration of hydrogen peroxide is obtained. The concentration of hydrogen peroxide in the experiment vessel can be calculated from the volume of the experiment vessel and the concentration and quantity of the aqueous solution of hydrogen peroxide injected. The correlation thus obtained is always constant, and from this correlation can be obtained a constant conversion rate.

By this prior art, as described, the output of the semiconductor gas sensor can be converted at a constant conversion rate and shown on a concentration indicator. Thus, the concentration of hydrogen peroxide vapor in the treatment vessel can be known on a real-time basis. That is to say, the concentration of hydrogen peroxide vapor can be well controlled, and sterilization and disinfection operations can be carried out efficiently.

It was found, however, that the concentration determined by this prior art method could differ from the actual level of the hydrogen peroxide vapor in the treatment vessel and that no accurate measurement could be made of the concentration of the hydrogen peroxide vapor by the semiconductor gas sensor.

In an effort to solve this problem, the inventors conducted various experiments and researches. It was discovered that even if the concentration of hydrogen peroxide vapor was kept at a constant level in the treatment vessel, the output of the sensor changes with changes in the temperature or humidity in the treatment vessel. The conversion rate for turning the output of the sensor into the hydrogen peroxide concentration was one based on the data worked out with the temperature and humidity maintained at a constant level in the experiment vessel as described. It was found that, in the actual sterilization and disinfection treatments in which temperatures and humidities are varied, the value obtained by converting the sensor output at the aforesaid conversion rate could be different from the actual hydrogen peroxide vapor concentration. The prior art method could not control the concentration correctly in such treatments as sterilization and disinfection, which in practice are performed under varying temperature or humidity conditions.

SUMMARY OF THE INVENTION

It is an object of the present invention to provide a method for the detection of a concentration of hydrogen peroxide vapor which always permits accurate detection on a real-time basis of the concentration of hydrogen peroxide vapor in the treatment vessel (in-vessel concentration) under varying in-vessel temperature or humidity conditions, thus ensuring efficient and effective sterilization and disinfection treatments. It is another object of the present invention to provide an apparatus for carrying out the above-mentioned method properly.

The method for detection of the concentration of hydrogen peroxide vapor according to the present invention is one which determines the in-vessel concentration by means of a semiconductor sensor in a treatment system so arranged that the object to be treated comes in contact with hydrogen peroxide vapor. To achieve the aforesaid objects, the present invention proposes detecting and indicating the concentration of hydrogen peroxide vapor especially in three different ways using three different types of apparatuses:

VARIABLE HUMIDRTY. The first way or the first method is applicable to treatments such as sterilization and disinfection which are performed in a treatment vessel with the pressure therein (in-vessel pressure) fixed, usually at atmospheric pressure, and the temperature therein (in-vessel temperature) maintained at a constant level but with the humidity therein (in-vessel humidity) varying. The output of the semiconductor gas sensor is arithmetically revised in relation to the in-vessel humidity on the basis of predetermined correlation data (humidity variable data) between the output of the semiconductor gas sensor and the concentration of hydrogen peroxide vapor in which the humidity is a parameter. The value thus revised is indicated on the concentration indicator as concentration of hydrogen peroxide vapor.

VARIABLE TEMPERATURE. The second method is for use in treatments such as sterilization and disinfection which are performed in an treatment vessel with the in-vessel pressure fixed, usually at the atmospheric pressure, and the in-vessel humidity maintained at a constant level, but with the in-vessel temperature varying. The output of the semiconductor gas sensor is arithmetically revised in relation to the in-vessel temperature on the basis of predetermined correlation data (temperature variable data) between the output of the semiconductor gas sensor and the concentration of hydrogen peroxide vapor in which the temperature is a parameter. The value thus revised is indicated on the concentration indicator as concentration of hydrogen peroxide vapor.

VARIABLE TEMPERATURE AND HUMIDITY. The third method is practiced in treatments such as sterilization and disinfection which are performed in an treatment vessel with the in-vessel pressure maintained at a constant level, usually the atmospheric pressure, but with the in-vessel temperature and humidity varying. The output of the semiconductor gas sensor is arithmetically revised in relation to the in-vessel temperature and humidity on predetermined correlation data (temperature-humidity variable data) between the output of the semiconductor gas sensor and the concentration of hydrogen peroxide vapor in which the temperature and the humidity are parameters. The value thus revised is indicated on the concentration indicator as concentration of hydrogen peroxide vapor.

The apparatus for detection of the concentration of hydrogen peroxide vapor in the first method (first type apparatus) comprises a semiconductor gas sensor to detect the in-vessel concentration, a humidity detector to detect the in-vessel humidity, an arithmetic unit to arithmetically revise the output of the semiconductor gas sensor on the basis of predetermined humidity variable data in relation to the in-vessel humidity detected by the humidity detector, and a concentration indicator to show the revised value obtained by the arithmetic unit as concentration of the hydrogen peroxide vapor.

The apparatus for detection of the concentration of hydrogen peroxide vapor in the second method (second apparatus type) comprises a semiconductor gas sensor to detect the in-vessel concentration, a temperature detector to detect the in-vessel temperature, an arithmetic unit to arithmetically revise the output of the semiconductor gas sensor on the basis of predetermined temperature variable data in relation to the in-vessel temperature detected by the temperature detector, and a concentration indicator to display the value obtained by the arithmetic unit as concentration of the hydrogen peroxide vapor.

The apparatus for detection of the concentration of hydrogen peroxide vapor in the third method (third apparatus type) comprises a semiconductor gas sensor to detect the in-vessel concentration, a temperature detector to detect the in-vessel temperature, a humidity detector to detect the in-vessel humidity, an arithmetic unit to arithmetically revise the output of the semiconductor gas sensor on the basis of predetermined temperature-humidity variable data in relation to the in-vessel temperature and the in-vessel humidity detected by the respective detectors, and a concentration indicator to display the arithmetically corrected value obtained by the arithmetic unit as concentration of the hydrogen peroxide vapor.

DESCRIPTION OF THE PREFERRED EMBODIMENTS

Figure 1:
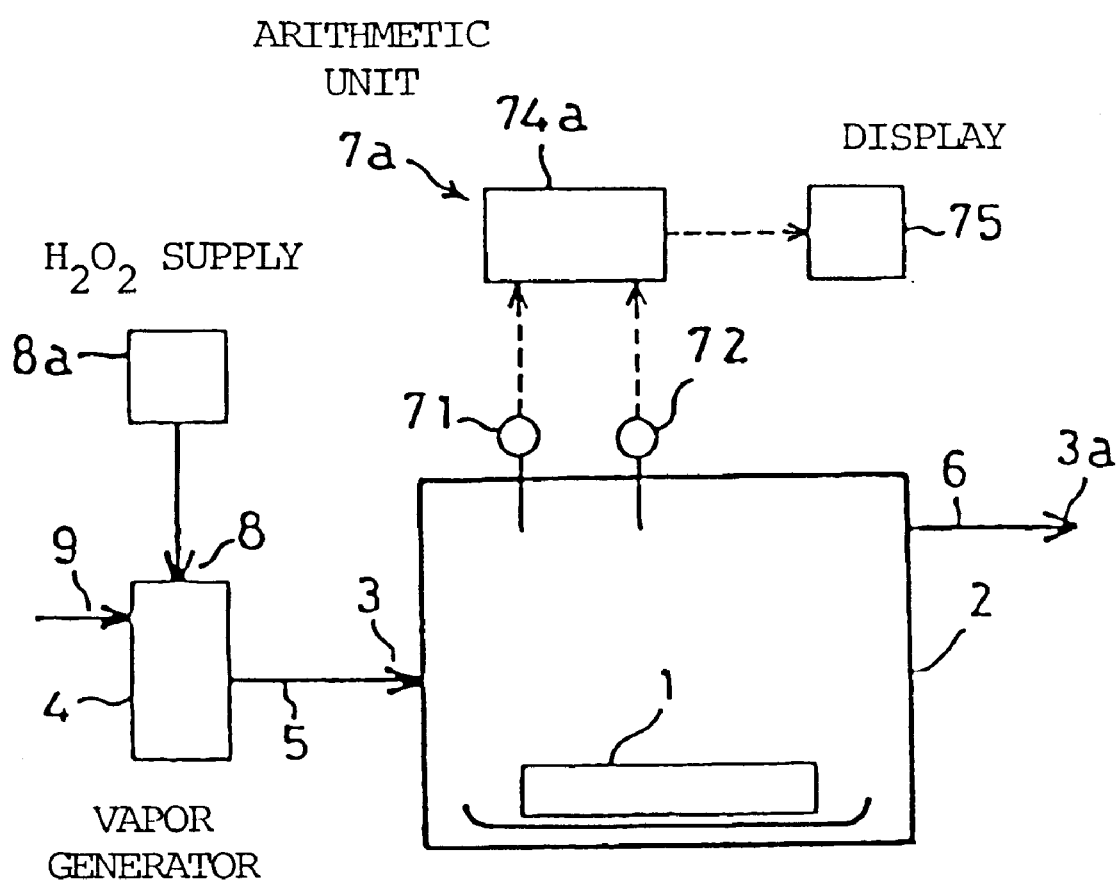
FIG. 1 is a schematic diagram showing an example of a sterilization system equipped with the first type apparatus.

The construction of the present invention will now be described in detail with reference to FIGS. 1 to 4 (first type apparatus), FIGS. 5 to 7 (second type apparatus), and FIGS. 8 to 10 (third type apparatus). These embodiments are concerned with examples where the present invention is applied to a sterilization and disinfection of such materials as pharmaceutical basic materials.

Example 1—Variable Humidity

FIGS. 1 to 4 show an embodiment of the first method and the first type apparatus. The system for treatment with hydrogen peroxide vapor shown in FIG. 1 comprises a treatment vessel 2 in which a object 1 to be treated as, for example, pharmaceutical basic materials is to be placed for sterilization, a hydrogen peroxide vapor generator 4 to produce hydrogen peroxide vapor 3, a supply line 5 to continuously supply hydrogen peroxide vapor 3 from the hydrogen peroxide vapor generator 4 to the treatment vessel 2, an exhaust line 6 to discharge into the atmosphere an exhaust gas 3a containing excessive hydrogen peroxide vapor from the treatment vessel 2, and a detection apparatus 7a which detects and indicates the concentration of hydrogen peroxide vapor in the treatment vessel 2 or the in-vessel concentration dx on a real-time basis. It is so arranged that the object 1 to be treated is brought into contact with hydrogen peroxide vapor 3 for sterilization in the treatment vessel 2 under the conditions with the humidity in the vessel (in-vessel humidity) varying but the pressure in the vessel (in-vessel pressure) and the temperature in the vessel (in-vessel temperature) both kept at a constant level.

The hydrogen peroxide vapor generator 4 is so designed as to heat and vaporize an aqueous solution of hydrogen peroxide 8 (concentration 31 percent by weight and specific gravity 1.1, for example) supplied from an aqueous hydrogen peroxide solution supply source 8a and mix the vaporized solution with a carrier air 9 to produce hydrogen peroxide vapor 3 as shown in FIG. 1. It is noted that the in-vessel concentration dx can be freely adjusted by regulating the rate of the flow of hydrogen peroxide vapor from the supply line 5 to the treatment vessel 2 or controlling the amount of hydrogen peroxide vapor generated at the hydrogen peroxide vapor generator 4. The exhaust line 6, not shown in the figure, is provided with an exhaust gas treatment unit where hydrogen peroxide contained in the exhaust gas 3a is rendered harmless with such a hydrogen peroxide decomposer as activated charcoal (to be diluted to the extent that the gas is harmless and can be released into the atmosphere—generally or preferably not higher than 1 ppm).

In the aforesaid sterilization treatment, the in-vessel pressure is generally maintained at atmospheric pressure and with the temperature kept at a constant point $t_F$ in a range between 20 and 50° C. The in-vessel humidity hx varies between 0.1 and 15 mg/l depending on the humidity of the carrier air 9 and the quantity 4 of the aqueous hydrogen peroxide solution 8 supplied to the hydrogen peroxide vapor generator for vaporization.

The apparatus for detection of the concentration of hydrogen peroxide vapor in the present embodiment or the first type apparatus 7a comprises, as shown in FIG. 1, a semiconductor gas sensor 71 to detect the in-vessel concentration dx, a humidity detector 72 to detect the in-vessel humidity hx, an arithmetic unit 74a where the detection signals are constantly input from the semiconductor gas sensor 71 and the humidity detector 72 and checked against the pre-stored humidity variable data Qx, and a concentration indicator 75 to display the concentration by the input signals from the arithmetic unit 74a.

The first type apparatus is so constructed that the sterilization in the present treatment system is carried out under the aforesaid conditions, i.e., with the in-vessel pressure fixed—atmospheric pressure—and the in-vessel temperature tr maintained at a constant level but with the in-vessel humidity hx varying and that the arithmetic unit 74a arithmetically revises the output of the semiconductor gas sensor 71 (the sensor output gx), in relation to the in-vessel humidity hx detected by the humidity detector 72, on the basis of the humidity variable data Qx, i. e., the correlation data between the output of the semiconductor gas sensor 71 and the concentration of hydrogen peroxide vapor in which the humidity is a parameter and then the concentration indicator 75 displays the arithmetically revised value as concentration of hydrogen peroxide vapor.

The semiconductor gas sensor 71 comprises a sensor element made of a sintered metal oxide which changes in electro-conductivity on contact with hydrogen peroxide vapor 3, electrodes embedded therein, and a means for heating the sensor element (indirect or direct heating type). That is, the principle is this: when the gas constituents are adsorbed on the surface of such oxide particles as n-type semiconductor oxides (e.g., $SnO_2$, ZnO, $V_2O_5$, $\gamma$-$Fe_2O_3$, $TiO_2$, and CdO) and p-type semiconductor oxides (e.g., NiO, $Cr_2O_3$, $Cu_2O$, $MnO_2$, and MnO) which form a sensor element, the free electrons near the surface move to change the electro-conductivity. This change in electro-conductivity is detected and utilized. The increase in electro-conductivity on contact with hydrogen peroxide vapor 3 or the drop in resistance is converted into the increase in voltage as in an electric circuit and is output. The sensor element is heated to accelerate the rate of adsorption of the object gas and oxygen to and desorption from the surface of the semiconductor to raise the gas detection response speed. The heating temperature is set generally or preferably at 200 to 400° C. The semiconductor sensor 71 used in the first type apparatus 7a may be a commercially available gas leakage detection sensor (for instance, Model 812, available from Figaro Giken Co., Ltd. of Japan) designed to detect alcohol and organic solvent gases. Gas sensor Model #812 has a sensor element made of sintered $SnO_2$ and may be heated to 350° C. by a nichrome wire heater arranged inside.

The humidity variable data Qx can generally be worked out in the following procedure: The same semiconductor gas sensor as the aforesaid gas sensor 71 is mounted in a suitable experiment vessel to which the aforementioned hydrogen peroxide vapor generator 4 is connected. To the hydrogen peroxide vapor generator 4 is injected by micro-syringe a specific quantity of aqueous solution of hydrogen peroxide (concentration 31 percent by weight, specific gravity 1.11), which is then completely evaporated by heating instantly by heater and mixed with a carrier air 9 to produce hydrogen peroxide vapor. A measurement is then taken of the output (data output) Gx of the semiconductor gas sensor mounted in the experiment vessel with the in-vessel humidity (data humidity) Hx, and the in-vessel temperature (data temperature) Tx maintained at a constant level under the atmospheric pressure. The concentration of hydrogen peroxide vapor (data concentration) Dx in this experiment vessel can be calculated accurately on the basis of the flow rate of the carrier air 9, the concentration, specific gravity and quantity injected of the aqueous hydrogen peroxide solution 8, because the vapor is produced by completely evaporating the aqueous hydrogen peroxide solution 8 injected into the hydrogen peroxide vapor generator 4.

Figure 2:
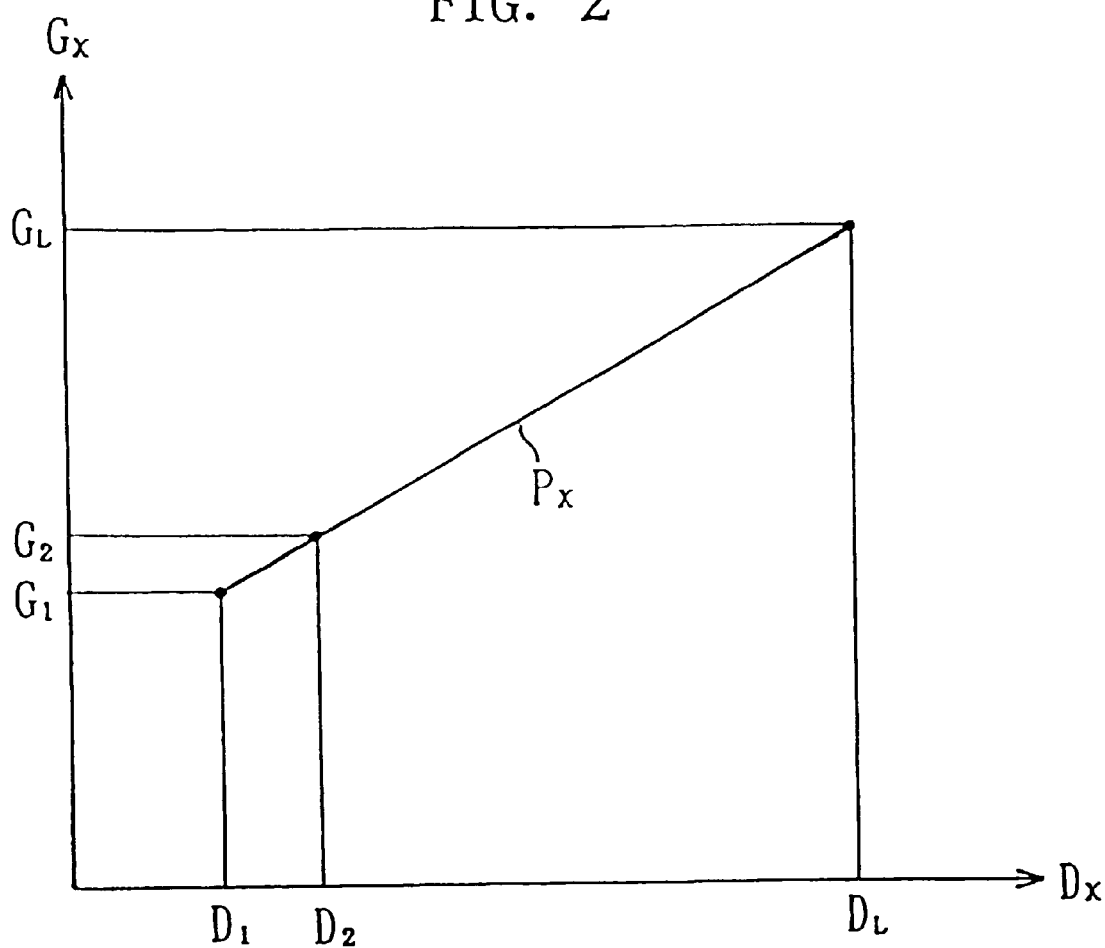
FIG. 2 is a two-way logarithmic graph showing a general example of the output-concentration conversion data with a constant humidity and a constant temperature.

With the flow rate of the carrier 9 maintained at a constant level, an amount of the aqueous hydrogen peroxide solution 8 as injected is varied in a plurality of stages (L stages). At each stage of injection, the aforesaid procedure (a series of steps from injection of the aqueous hydrogen peroxide solution 8 to detection of the data output) is repeated under the same conditions as stated above. Thus the correlation data (output-concentration conversion data) Px between data outputs $G_1$, $G_2$ ... $G_L$ and data concentrations $D_1$, $D_2$ ... $D_L$ at a specific data humidity Hx and a specific data temperature Tx is obtained. If this correlation between data outputs $G_1$, $G_2$ ... $G_L$ and data concentrations $D_1$, $D_2$ ... $D_L$ in the output-concentration conversion data Px is presented in a two-way logarithmic graph with the data output Gx on the axis of ordinates and the data concentration Dx on the axis of abscissas on the logarithmic scale, Px will be linear with an almost fixed gradient as shown in FIG. 2. The range within which an amount of the aqueous hydrogen peroxide solution as injected is varied is so selected that the range ($D_1 \leq D_x \leq D_L$) of varying of the data concentration Dx to be calculated therefrom agrees with or includes the predicted range ($d_1 \leq d_x \leq d_L$) of variability of the in-vessel concentration dx in the present treatment, that is to say, $D_1 \leq d_1$, $D_L \geq d_L$.

In the next step, by changing the humidity of the carrier air 9, the data humidity Hx is sequentially changed at a minute value interval in a plurality of stages (N stages) with the data temperature Tx maintained at a constant temperature $T_F$ identical with the constantly maintained in-vessel temperature $t_F$ and with the varying range ($H_1 \leq Hx \leq H_N$) of the data humidity Hx tallying with or including the predicted range of variability of the in-vessel humidity hx ($h_1 \leq hx \leq h_N$), that is $H_1 \leq h_1$, $H_N \leq h_N$. At different data humidities $H_1$, $H_2$ ... $H_N$ is worked out the output-concentration conversion data $P_1$, $P_2$ ... $P_N$ in the same manner as shown above, from which the humidity variable data Qx are obtained.

Figure 3:
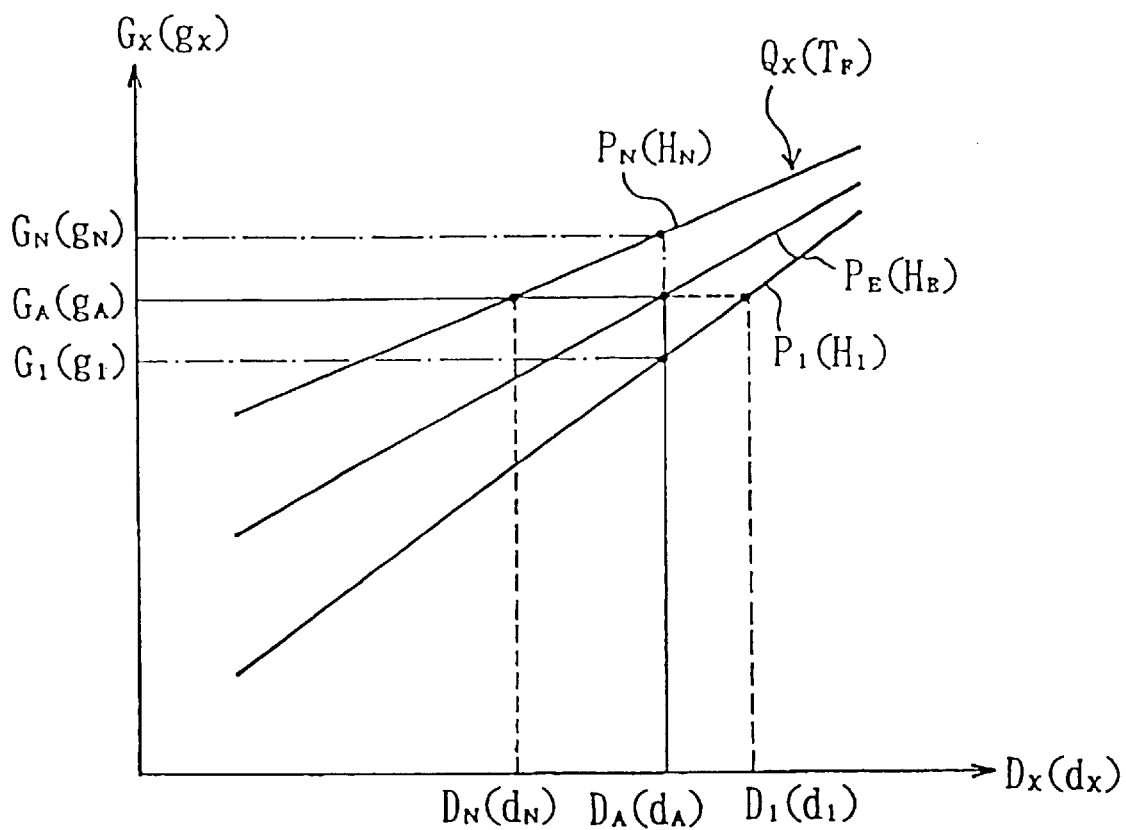
FIG. 3 is a two-way logarithmic graph showing a general example of the humidity variable data.

In other words, the humidity variable data Qx is made up of N items of the output-concentration conversion data $P_1$, $P_2$ ... with the humidity varying within a specific humidity range ($H_1 \leq Hx \leq H_N$) at a specific temperature (Tx=$T_F$=$t_F$= constant). The correlation between the data output $G_1$, $G_2$ ... and the data concentration $D_1$, $D_2$ ... at each of the output-concentration data $P_1$, $P_2$ ... $P_N$ making up the humidity variable data Qx is shown in the aforesaid two-way logarithmic graph. As shown in FIG. 3, the gradient is roughly linear. It is noted that the gradients of the respective output-concentration conversion data $P_1$, $P_2$ ... $P_N$ are generally not identical and that the humidity variable data Qx are represented by N items of different straight lines with different gradients as shown in FIG. 3. The respective straight lines indicate the output-concentration conversion data $P_1$, $P_2$ ... $P_N$ at the respective data humidities $H_1$, $H_2$ ... $H_N$. In FIG. 3 only the output-concentration conversion data $P_1$, $P_E$, and $P_N$ at the data humidities $H_1$, $H_E$, and $H_N$ ($H_1 < H_E < H_N$) are presented, for the sake of convenience.

Figure 4:
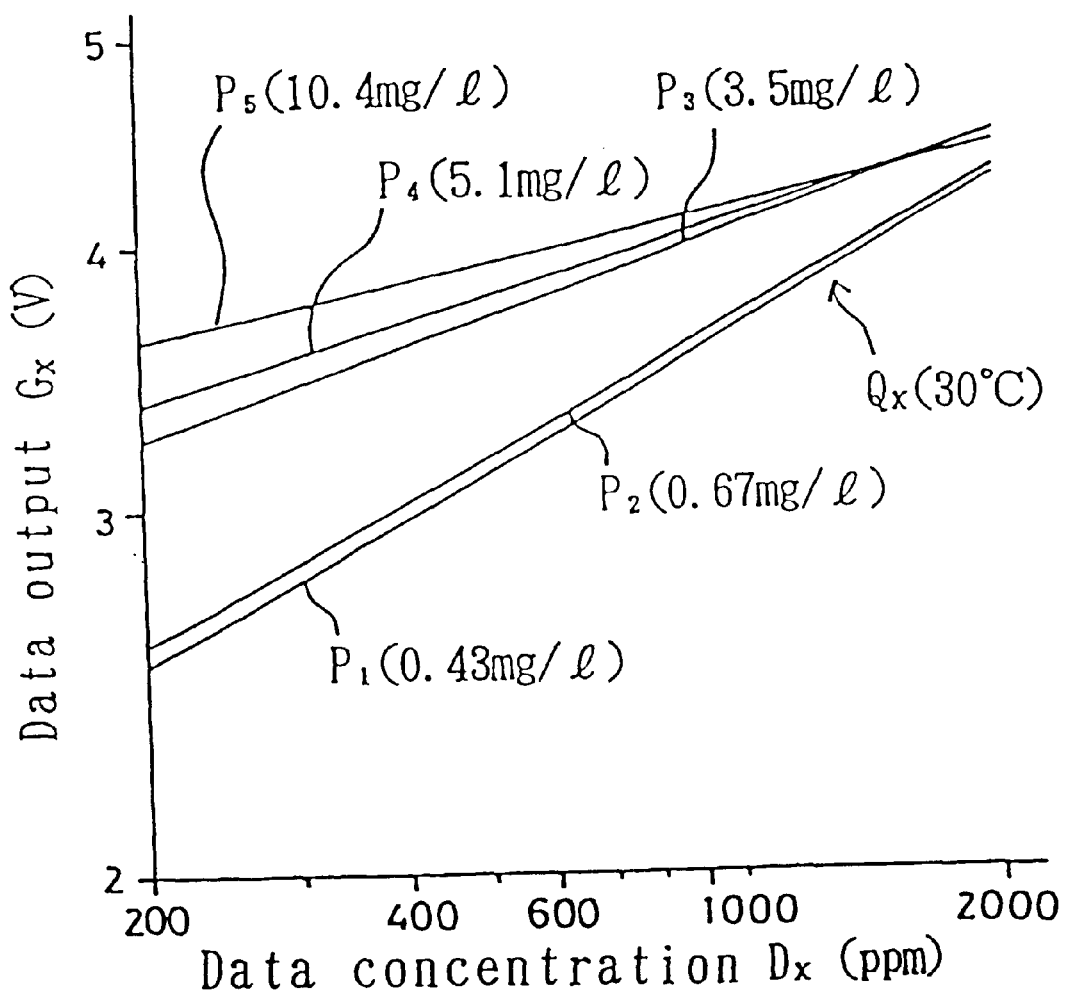
FIG. 4 is a two-way logarithmic graph showing a specific example of the humidity variable data.

As a concrete example, FIG. 4 shows, for instance, part of the humidity variable data Qx to be stored in the arithmetic unit 74a in the case in which sterilization is carried out in the aforementioned treatment system with an in-vessel pressure of atmospheric pressure, an in-vessel temperature of 30° C., an in-vessel humidity of 0.1 to 15 mg/liter and an in-vessel concentration of 200 to 2,000 ppm. That is a presentation in an two-way logarithmic graph of the output-concentration conversion data $P_1$, $P_2$, $P_3$, $P_4$, and $P_5$ at a data humidity Hx of 0.43 mg/liter, 0.67 mg/liter, 3.5 mg/liter, 5.1 mg/liter, and 10.4 mg/liter. Measurements were made under the following conditions and using the following procedures: the experiment vessel was a plastic vessel with a capacity of 136 liters; the aqueous solution of hydrogen peroxide injected into the hydrogen peroxide vapor generator 4 was an aqueous hydrogen peroxide solution with a concentration of 31% and a specific gravity of 1.11; the semiconductor gas sensor mounted in the experiment vessel was a Model 812 obtained from Figaro Giken Go., Ltd. of Japan. With the in-vessel pressure maintained at atmospheric pressure and the temperature maintained at 30° C., the humidity in the experiment vessel was changed in five stages: 0.43 mg/liter, 0.67 mg/liter, 3.5 mg/liter, 5.1 mg/liter, and 10.4 mg/liter. At each humidity level, the concentration of hydrogen peroxide vapor in the experiment vessel was changed within the range between 200 and 2,000 ppm and the output of the semiconductor gas sensor was measured. The measurements were then plotted in a two-way logarithmic graph.

Detection and indication of the in-vessel concentration dx by the first type apparatus 7a are effected according to the first method by the arithmetic unit 74a with the humidity variable data Qx stored therein and the concentration indicator 75 as follows:

The in-vessel humidity hx is first detected by the humidity detector 72. From the humidity variable data Qx is selected the output-concentration conversion data $P_E$ obtained at the data humidity $H_E$ corresponding to the detected humidity $h_E$. From this output-concentration conversion data $P_E$, the data concentration $D_A$ in correlation with the data output $G_A$ corresponding to the sensor output $g_A$ is picked out, as shown in FIG. 3. The value (arithmetically revised) corresponding to this data concentration $D_A$ is displayed as the concentration of hydrogen peroxide vapor $d_A$ on the indicator 75. Thus, the in-vessel concentration $d_A$ can be determined accurately.

Unless the in-vessel humidity hx is fixed, it can happen that the sensor output $g_A$ will not change even when the in-vessel concentration dx changes. In such cases, too, a correct output-concentration conversion data is selected in accordance with change in the in-vessel humidity hx, and an accurate in-vessel concentration dx is indicated on the concentration indicator 75. If, for example, the in-vessel humidity hx changes from $h_E$ to $h_1$ (or $h_N$), this will be detected by the humidity detector 72, and the output-concentration conversion data $P_1$ (or $P_N$) obtained at the data humidity $H_1$ (or $H_N$) corresponding to the detected humidity $h_1$ (or $h_N$) will be selected anew. From this output-concentration conversion data $P_1$ (or $P_N$) will be picked out the data concentration $D_1$ (or $D_N$) in correlation with the data output $G_A$ corresponding to the sensor output $g_A$, as shown in FIG. 3. The value corresponding to this data concentration $D_1$ (or $D_N$) will be indicated on the concentration indicator 75 as the concentration of hydrogen peroxide vapor $d_1$ (or $d_N$). In this manner, the change of the in-vessel concentration dx from $d_A$ to $d_1$ (or $d_N$) is accurately reflected on the concentration indictor 75.

Conversely, it can happen that when the in-vessel humidity hx changes instead while the in-vessel concentration dx remains unchanged, the sensor output gx can change. In such a case, too, the correct output-concentration conversion data will be picked out in accordance with change in the in-vessel humidity hx, with the concentration reading remaining unchanged on the concentration indicator 75. For instance, if the sensor output gx shifts from $g_A$ to $g_1$ (or $g_N$) with the in-vessel humidity hx changing from $h_E$ to $h_1$ (or $h_N$), there will be picked out a new the output-concentration data $P_1$ (or $P_N$) obtained at the data humidity $H_1$ (or $H_N$) corresponding to the humidity $h_1$ (or $h_N$) detected by the humidity detector 72. From this output-concentration conversion data $P_1$ (or $P_N$) is picked out the data concentration $D_A$ in correlation with the data output $G_1$ (or $G_N$) corresponding to the sensor output $g_1$ (or $g_N$) as shown in FIG. 3. The value corresponding to this data concentration $D_A$ is indicated as the concentration of hydrogen peroxide vapor $d_A$ on the concentration indicator 75. Thus, that the in-vessel concentration $d_A$ has not changed will be accurately reflected on the concentration indicator 75.

This conversion of the sensor output gx into the hydrogen peroxide vapor concentration on the basis of the humidity variable data Qx is carried out through a comparison calculation between the sensor output gx and the detected humidity hx and the humidity variable data Qx stored in the operator 74a, where a value equal or most approximate to the in-vessel concentration dx is picked out in an arithmetic calculation. Therefore, the difference between the arithmetically calculated value and the in-vessel concentration dx can be minimized by working out a further accurate humidity variable data Qx, i.e., by increasing, to the largest possible extent, the number N of the output-concentration conversion data $P_1$, $P_2$ ... $P_N$ which make up the humidity variable data Qx and the detection number L of the data output and the data concentration at the respective output-concentration conversion data $P_1$, $P_2$ ... $P_N$.

In the meantime, the hydrogen peroxide vapor in the treatment vessel 2 is chemically adsorbed on the oxide semiconductor element in the semiconductor gas sensor 71. Then, the free electrons are moved in the element, increasing the electro-conductivity. The reaction starts very fast, and thus the sensor output gx quickly reflects the change in the in-vessel concentration dx.

This shows that the first method using the first type apparatus 7a permits direct and real-time accurate detection of the in-vessel concentration dx even under the conditions where the in-vessel humidity hx fluctuates. Thus, the in-vessel concentration dx can be controlled with ease and properly, and the sterilization and disinfection of such objects 1 to be treated as pharmaceutical basic materials can be carried out efficiently and effectively.

Example 2—Variable Temperature

Figure 5:
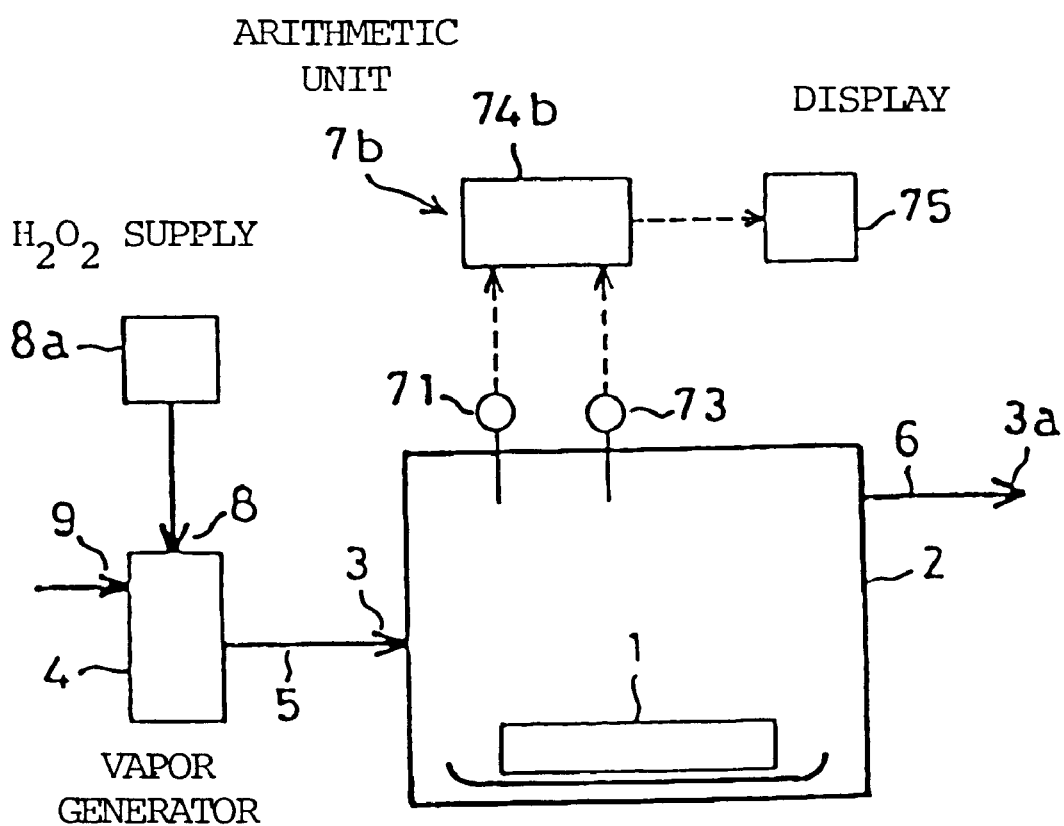
FIG. 5 is a schematic diagram showing an example of a sterilization system provided with the second type apparatus.
Figure 6:
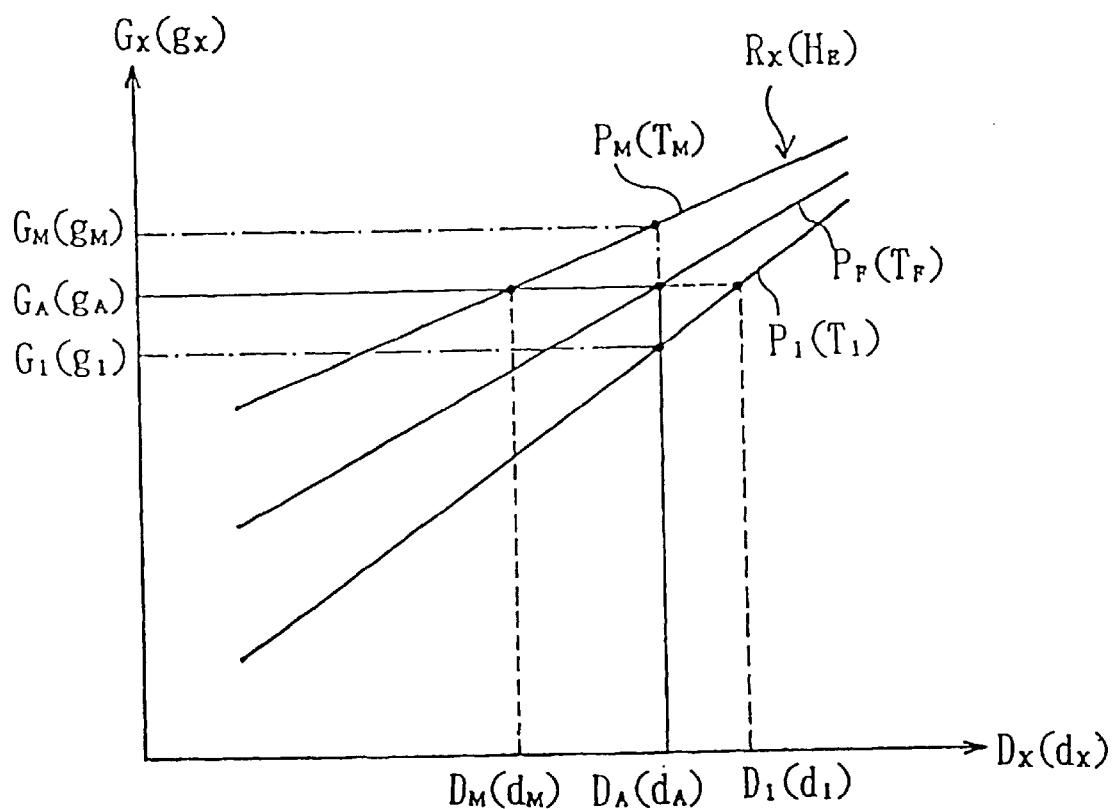
FIG. 6 is a two-way logarithmic graph showing a general example of the temperature variable data.
Figure 7:
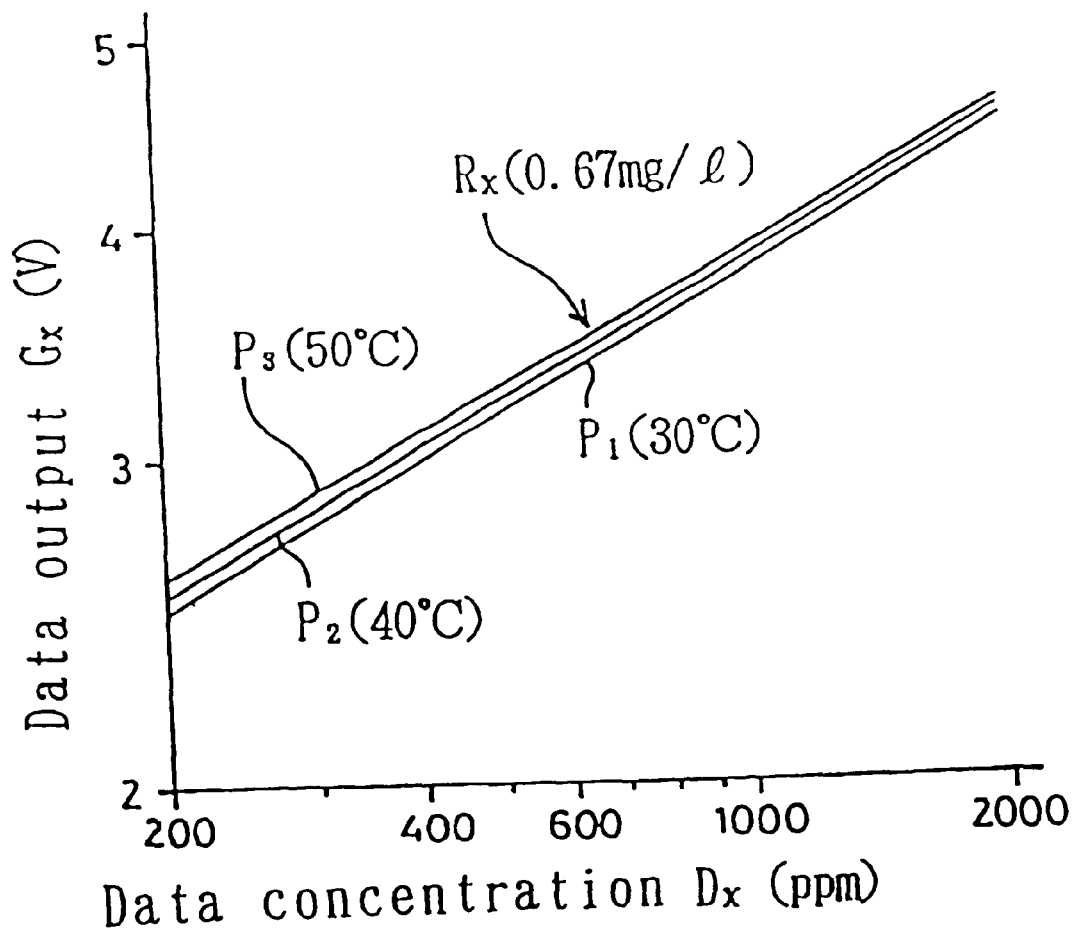
FIG. 7 is a two-way logarithmic graph showing a specific example of the temperature variable data.

FIGS. 5 to 7 illustrate an embodiment of the second method and the second type apparatus. The system for treatment with hydrogen peroxide vapor shown in FIG. 5 comprises a treatment vessel 2, a hydrogen peroxide vapor generator 4, a supply line 5, an exhaust line 6, and a hydrogen peroxide vapor concentration detection apparatus 7b, and is identical in arrangement with that in Example 1 except for the sterilization conditions (in-vessel pressure, in-vessel temperature, and in-vessel humidity) and the construction of the hydrogen peroxide vapor concentration detection apparatus 7b. That is to say, this treatment system is so arranged that the object 1 to be treated, such as pharmaceutical basic material, is brought into contact with hydrogen peroxide vapor 3 for sterilization in the treatment vessel 2 under the conditions that the in-vessel temperature tx varies, but with the in-vessel pressure and the in-vessel humidity both fixed. Generally, the in-vessel pressure is kept at atmospheric pressure and the in-vessel humidity is fixed at a constant point $h_E$ between 0.1 and 15 mg/liter. The in-vessel temperature tx can fluctuate between 20 and 50° C. depending on the treatment conditions.

The apparatus for detection of the concentration of hydrogen peroxide vapor in the present embodiment (the second type apparatus) 7b comprises, as shown in FIG. 5, a semiconductor gas sensor 71 to detect the in-vessel concentration dx, a temperature detector 73 to detect the in-vessel temperature tx, an arithmetic unit 74b where the detection signals are constantly input from the semiconductor gas sensor 71 and the temperature detector 73 and checked against the pre-stored temperature variable data Rx in a comparison calculation, and a concentration indicator 75 to display the concentration by the input signals from the arithemetic unit 74b. The second type apparatus is constructed so that where the sterilization in the present treatment system is carried out under the aforesaid conditions (in-vessel pressure fixed at atmospheric pressure and in-vessel humidity $h_E$ maintained at a constant level but with the in-vessel temperature tx varying), arithmetic unit 74b arithmetically revises the output of semiconductor gas sensor 71 (the sensor output gx) in relation to the in-vessel temperature tx detected by temperature detector 73 on the basis of the temperature variable data Rx, i.e., the correlation data between the output of semiconductor gas sensor 71 and the concentration of hydrogen peroxide vapor in which the temperature is a parameter and then the concentration indicator 75 shows the arithmetically revised value as concentration of hydrogen peroxide vapor. Semiconductor gas sensor 71 and concentration indicator 75 are the same ones as those used in the first type apparatus 7a.

The temperature variable data Rx can generally be worked out in the same way as the humidity variable data Qx: The data temperature Tx is sequentially changed at a minute value interval in a plurality of stages (M stages) with the data humidity Hx maintained at a constant level $H_E$ identical with the constantly maintained in-vessel humidity $h_E$ and with the varying range of the data temperature Tx ($T_1 \leq Tx \leq T_M$) tallying with or including the predicted range of variability of the in-vessel temperature tx ($t_1 \leq tx \leq t_M$) (generally 20° C.$\leq$tx$\leq$50° C), that is, $T_1 \leq t_1$, $T_M \geq t_M$. At different data temperatures $T_1$, $T_2$ . . . $T_M$ the output-concentration conversion data $P_1$, $P_2$ . . . $P_M$ is worked out in the same manner as shown above, from which the temperature variable data Rx are obtained. In other words, M items of the output-concentration conversion data $P_1$, $P_2$ . . . $P_M$ will be the temperature variable data Rx in the event that the temperature varies within a specified temperature range ($T_1 \leq Tx \leq T_M$) at a specific humidity condition (Hx=$H_E$=$h_E$=constant). The correlation between the data output $G_1$, $G_2$ . . . $G_M$ and the data concentration $D_1$, $D_2$ . . . $D_M$ at each of the output-concentration conversion data $P_1$, $P_2$ . . . $P_M$ making up the temperature variable data Rx is shown in the aforesaid two-way logarithmic graph. As shown in FIG. 6, the gradient is roughly linear. It is noted that the gradients of the respective output-concentration conversion data $P_1$, $P_2$ . . . $P_M$ are generally not identical and that the temperature variable data Rx are represented by M items of different straight lines with different gradients as shown in FIG. 6.

The respective straight lines indicate the output-concentration conversion data $P_1$, $P_2$ . . . $P_M$ at the respective data temperatures $T_1$, $T_2$ . . . $T_M$. In FIG. 6, only the output-concentration conversion data $P_1$, $P_F$, and $P_M$ obtained at the data temperatures $T_1$, $T_F$, and $T_M$ ($T_1 < T_F < T_M$) are presented, for the sake of convenience.

As a concrete example, FIG. 7 shows part of the temperature variable data Rx to be stored in the arithmetic unit 74b in the case where sterilization is carried out in the aforementioned treatment system under the conditions: the in-vessel pressure of atmospheric pressure, an in-vessel humidity of 0.67 mg/liter, an in-vessel temperature of 20 to 50° C., and an in-vessel concentration of 200 to 2,000 ppm. That is, a presentation in an two-way logarithmic graph of the output-concentration conversion data $P_1$, $P_2$ . . . $P_M$ at a data temperature Tx of 30° C., 40° C., and 50° C. Measurements were made under the following conditions and using the following procedures: the experiment vessel was a plastic vessel with a capacity of 136 liters; the aqueous solution of hydrogen peroxide injected into the hydrogen peroxide vapor generator 4 was aqueous hydrogen peroxide with a concentration of 31% and a specific gravity of 1.11; and the semiconductor gas sensor mounted in the experiment vessel was a Model 812 from Figaro Giken Go., Ltd. of Japan. With the in-vessel pressure at atmospheric pressure and the humidity maintained at 0.67 mg/liter, the temperature in the experiment vessel was changed in three stages of 30° C., 40° C., and 50° C. At each temperature, the concentration of hydrogen peroxide vapor in the experiment vessel was changed in the range between 200 and 2,000 ppm and the output of the semiconductor gas sensor was measured. The measurements were then plotted in a two-way logarithmic graph.

Detection and indication of the in-vessel concentration dx by the second type apparatus 7b are effected according to the second method by the arithmetic unit 74b with the obtained temperature variable data Rx stored therein and the concentration indicator 75 as follows:

The in-vessel temperature tx is first detected by the temperature detector 73. From the temperature variable data Rx is selected the output-concentration conversion data $P_F$ obtained at the data temperature $T_F$ corresponding to the detected temperature $t_F$. From this output-concentration conversion data $P_F$ is picked out the data concentration $D_A$ in correlation with the data output $G_A$ corresponding to the sensor output $g_A$ as shown in FIG. 6. The value (revised) corresponding to this data concentration $D_A$ is indicated as the concentration of hydrogen peroxide vapor $d_A$ on the concentration indicator 75. As shown, the in-vessel concentration $d_A$ can be determined accurately.

Unless the in-vessel temperature tx is fixed, it can happen that the sensor output $g_A$ will not change even when concentration dx changes. Even in such cases, a correct output-concentration conversion data is selected in accordance with the change in the in-vessel temperature tx, and an accurate in-vessel concentration dx is indicated on the concentration indicator 75. If, for example, the in-vessel temperature tx changes from $t_F$ to $t_1$ (or $t_M$), this will be detected by the temperature detector 73, and the output-concentration conversion data $p_1$ (or $P_M$) obtained at the data temperature $T_1$ (or $T_M$) corresponding to the detected temperature $t_1$ (or $t_M$) will be selected anew. From this output-concentration conversion data $P_1$ (or $P_M$) the data concentration $D_1$ (or $D_M$) in correlation with the data output $G_A$ corresponding to the sensor output $g_A$ will be picked out, as shown in FIG. 6. The value corresponding to this data concentration $D_1$ (or $D_M$) will be indicated on the concentration indicator 75 as the concentration of hydrogen peroxide vapor $d_1$ (or $d_M$). That is, the change of the in-vessel concentration dx from $d_A$ to $d_1$ (or $d_M$) is accurately reflected on the concentration indictor 75.

Conversely, when the in-vessel temperature tx changes while the in-vessel concentration dx remains unchanged, it can happen that the sensor output gx changes. In such a case, too, the correct output-concentration conversion data will be picked out in accordance with the change in the in-vessel temperature tx, with the concentration reading remaining unchanged on the concentration indicator 75. If, for example, the in-vessel temperature tx changes from $t_F$ to $t_1$ (or $t_M$) with the sensor output gx shifting from $g_A$ to $g_1$ (or $g_M$), there will be picked out anew the output-concentration data $P_1$ (or $P_M$) obtained at the data temperature $T_1$ (or $T_M$) corresponding to the temperature $t_1$ (or $t_M$) detected by the temperature detector 73. The data concentration $D_A$ is obtained from this output-concentration conversion data $p_1$ (or $p_M$) in correlation with the data output $G_1$ (or $G_M$) corresponding to the sensor output $g_1$ (or $g_M$), as shown in FIG. 6. The value corresponding to this data concentration $D_A$ is displayed as the concentration of hydrogen peroxide vapor $d_A$ on concentration indicator 75. Thus, the fact that the in-vessel concentration $d_A$ has not changed will be accurately reflected on concentration indicator 75.

This conversion of the sensor output gx into the hydrogen peroxide vapor concentration on the basis of the temperature variable data Rx is carried out through a comparison between the sensor output gx and the detected temperature tx, and the temperature variable data Rx stored in arithmetic unit 74b, where a value equal or most approximate to the in-vessel concentration dx is obtained in an arithmetic calculation. Therefore, the difference between the arithmetically calculated value and the in-vessel concentration dx can be minimized by working out a further accurate temperature variable data Rx, i.e., by increasing, to the largest possible extent, the number N of the output-concentration conversion data $P_1$, $P_2$ ... $P_N$ which make up the temperature variable data Rx and the number L of detecting the data output and the data concentration at the respective output-concentration conversion data $P_1$, $P_2$ ... $P_N$.

This demonstrates that as in the first method, the second method using the second type apparatus 7b permits direct and real-time accurate detection of the in-vessel concentration dx even under conditions in which the in-vessel temperature tx fluctuates. Thus, the in-vessel concentration dx can be controlled with ease, and sterilization and disinfection of objects 1 to be treated, such as pharmaceutical basic materials, can be carried out efficiently and effectively.

Example 3—Variable Humidity and Temperature

Figure 8:
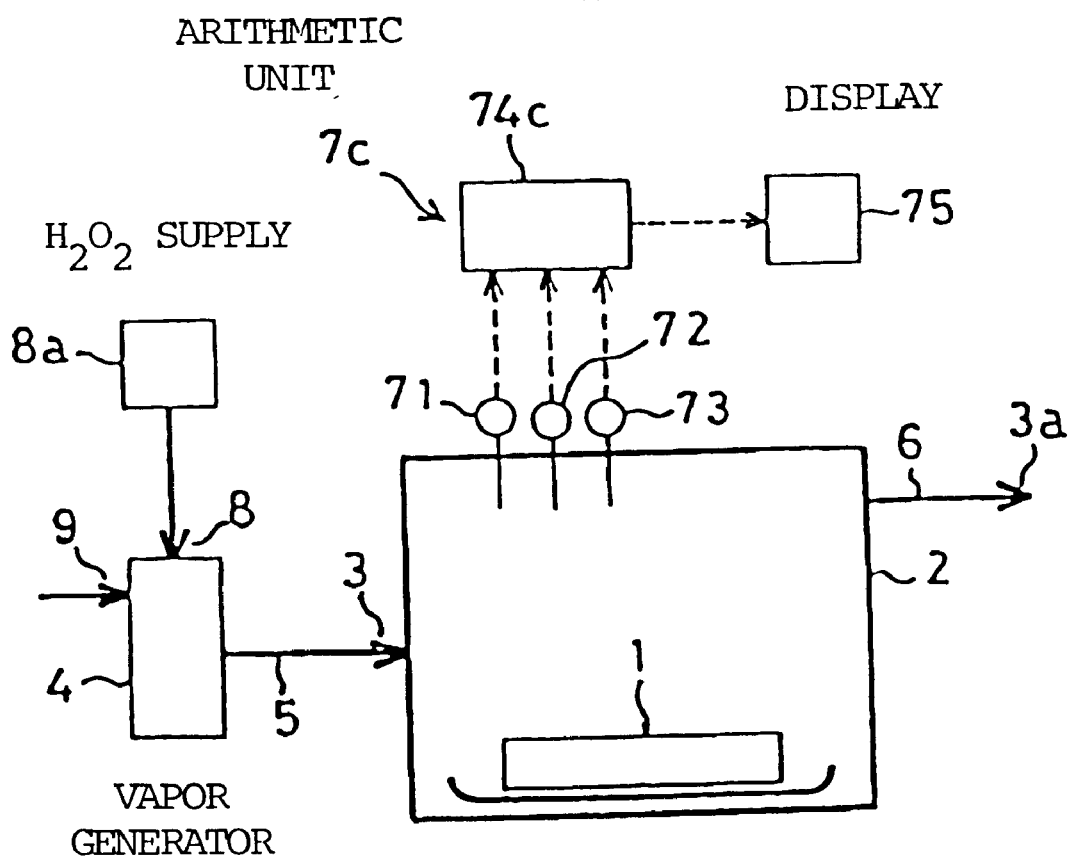
FIG. 8 is a schematic diagram showing an example of a sterilization system provided with the third type apparatus.
Figure 9:
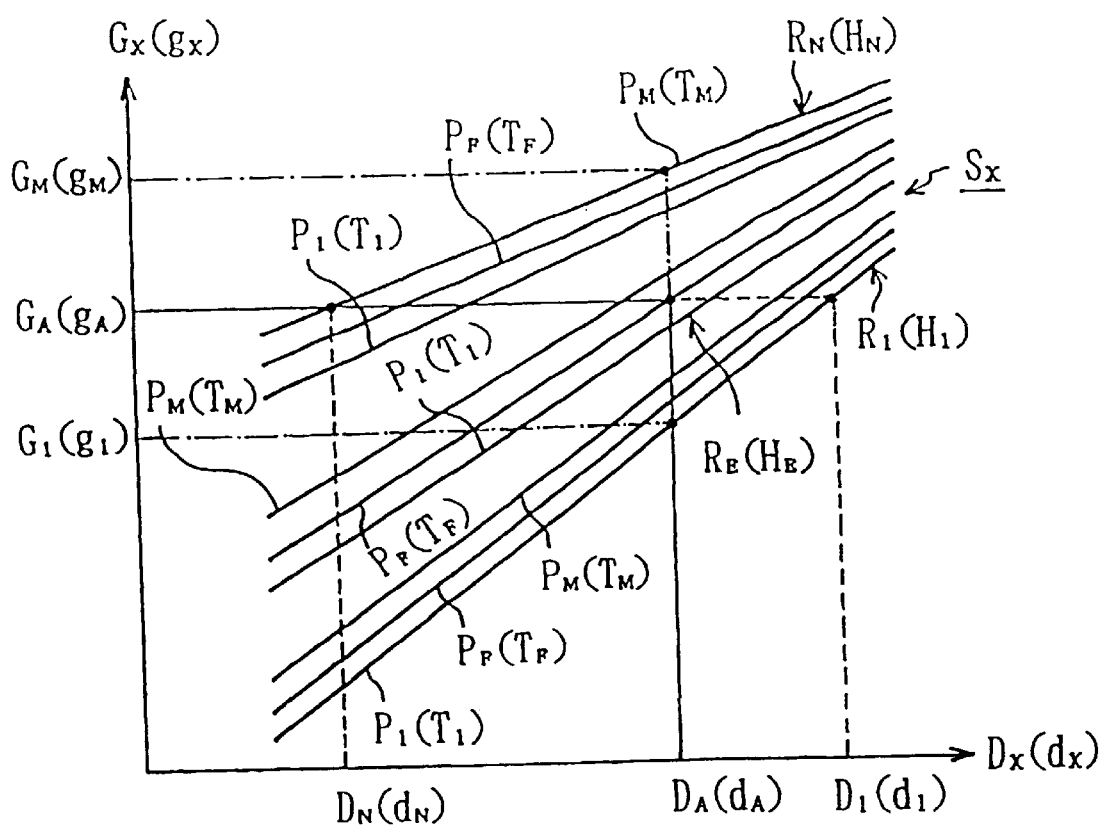
FIG. 9 is a two-way logarithmic graph showing a general example of the temperature-humidity variable data.
Figure 10:
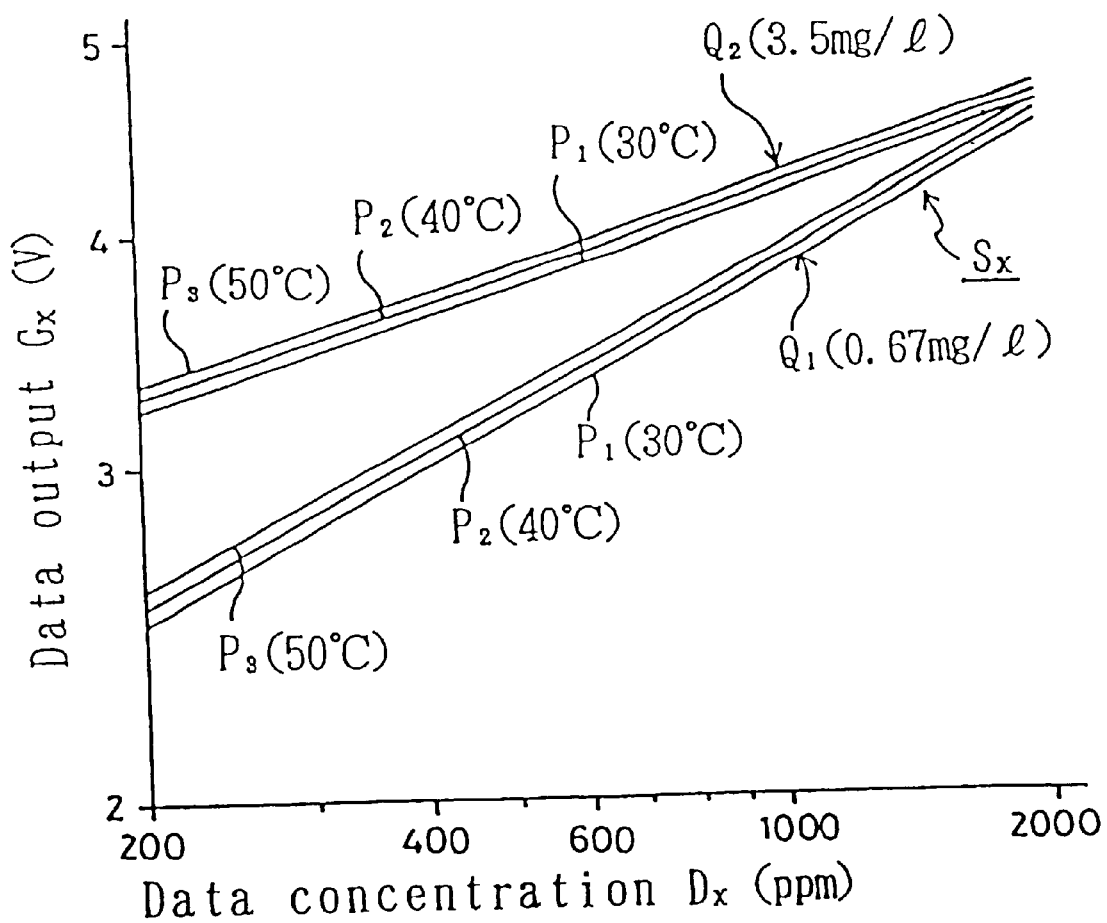
FIG. 10 is a two-way logarithmic graph showing a specific example of the temperature-humidity variable data.

An embodiment of the third method and the third type apparatus is shown in FIGS. 8 to 10. The system for treatment with hydrogen peroxide vapor shown in FIG. 8 is equipped with a treatment vessel 2, a hydrogen peroxide vapor generator 4, a supply line 5, an exhaust line 6, and a hydrogen peroxide vapor concentration detection apparatus 7c. It is identical in arrangement with the system in the foregoing examples except for the sterilization conditions (in-vessel pressure, in-vessel temperature, and in-vessel humidity) and the construction of the hydrogen peroxide vapor concentration detection apparatus 7c. That is to say, this treatment system is so arranged that the object 1 to be treated, for instance, a pharmaceutical basic material, is brought into contact with hydrogen peroxide vapor 3 for sterilization in treatment vessel 2 under conditions such that the in-vessel pressure is maintained at a constant level, but the humidity hx and the temperature tx are varying. Generally, the in-vessel pressure is fixed at atmospheric pressure, but the in-vessel humidity changes between 0.1 and 15 mg/liter and the in-vessel temperature tx fluctuates within a range between 20 and 50° C., depending on the treatment conditions.

The apparatus for detection of the concentration of hydrogen peroxide vapor in the present embodiment or the third type apparatus 7c comprises, as shown in FIG. 8, a semiconductor gas sensor 71 to detect the in-vessel concentration dx, a humidity detector 72 to detect the in-vessel humidity hx, a temperature detector 73 to detect the in-vessel temperature tx, an arithmetic unit 74c where the detection signals are constantly input from the semiconductor gas sensor 71 and the two detectors 72 and 73 and checked against the pre-stored temperature-humidity variable data Sx in a comparative calculation, and a concentration indicator 75 to display the concentration by the signals input from the arithmetic unit 74c. The third type apparatus is constructed so that, where sterilization in the present treatment system is carried out under the aforesaid conditions, that is, with the in-vessel pressure maintained at a constant level atmospheric pressure but with the humidity hx and the temperature tx varying, the arithmetic unit 74c arithmetically revises the output of the semiconductor gas sensor 71 (the sensor output gx) in relation to the in-vessel humidity hx and the in-vessel temperature tx detected by the respective detectors 72 and 73, on the basis of the temperature-humidity variable data Sx, which is the correlation data between the output of the semiconductor gas sensor 71 and the concentration of hydrogen peroxide vapor in which the humidity and the temperature are parameters and then the concentration indicator 75 shows the arithmetically revised value as concentration of hydrogen peroxide vapor. The semiconductor gas sensor 71, the two detectors 72 and 73, and the concentration indicator 75 are the same ones as those used in the first and second type apparatuses 7a and 7b.

The temperature-humidity variable data Sx, which is stored in the arithmetic unit 74c and is composed of a group of temperature variable data or humidity variable data, is obtained by working out each temperature variable data or humidity variable data in the same way as mentioned earlier. That is, the temperature-humidity variable data Sx comprising a group of temperature variable data is obtained in the following procedure: First, the data humidity Hx is sequentially changed at a minute interval in a plurality of stages (N stages) within a range ($H_1 \leq Hx \leq H_M$) tallying with or including the predicted range of variability of the in-vessel humidity hx ($h_1 \leq hx \leq h_M$), that is $H_1 \leq h_1$, $H_M \geq h_M$. The temperature variable data $R_1$, $R_2$ ... $R_N$ are worked out at different data humidities data $H_1$, $H_2$ ... $H_N$. The respective temperature variable data $R_1$, $R_2$ ... $R_N$ can be obtained in the same procedure as that for the aforesaid temperature variable data Rx: The data temperature Tx is changed at a proper minute interval in a number of stages (M stages) within a range ($T_1 \leq Tx \leq T_M$) tallying with or including the predicted range of variability of the in-vessel temperature tx ($t_1 \leq tx \leq t_M$), that is $T_1 \leq t_1$, $T_M \geq t_M$. At different data $T_1$, $T_2$ ... $T_N$ temperatures the output-concentration conversion data $P_1$, $P_2$ ... $P_N$ are worked out. The N items of temperature variable data $R_1$, $R_2$ ... $R_N$ each of them comprising M items of out-concentration conversion data $P_1$, $P_2$ ... $P_N$, make up the temperature-humidity variable data Sx with temperature and humidity changing within the specific ranges ($T_1 \leq Tx \leq T_M$ and $H_1 \leq Hx \leq H_M$). The respective temperature variable data $R_1$, $R_2$ ... $R_N$ which make up the temperature-humidity variable data Sx are presented in the aforesaid two-way logarithmic graph. As shown in FIG. 9, the data are represented by M items of different straight lines with different gradients like the aforementioned temperature variable data Rx. The respective straight lines indicate the output-concentration conversion data $P_1, P_2 \ldots P_M$ at the respective data temperatures $T_1, T_2 \ldots T_M$. In FIG. 9, only the temperature variable data $R_1, R_E, R_M$ are presented, with the data humidities being $H_1, H_E,$ and $H_N$ ($H_1 < H_E < H_N$). Only the output-concentration conversion data $P_1, P_F,$ and $P_M$, with the data temperatures being $T_1, T_E,$ and $T_N$ ($T_1 < T_E < T_N$), are shown with regard to the respective temperature variable data $R_1, R_E,$ and $R_N$.

The temperature-humidity variable data can also be obtained by the following procedure: The data temperature Tx is sequentially changed at a minute value interval in a number of stages (M stages) within a range ($T_1 \leq Tx \leq T_M$) tallying with or including the predicted range of variability of the in-vessel temperature tx ($t_1 \leq tx \leq t_M$), that is $T_1 \leq t_1$, $T_M \geq t_M$. At different data temperatures $T_1, T_2 \ldots T_M$, the humidity variable data $Q_1, Q_2 \ldots Q_M$ are worked out. The respective humidity variable data $Q_1, Q_2 \ldots Q_M$ can be obtained in the same procedure as that for the aforesaid humidity variable data Qx: The data humidity Hx is sequentially changed at a minute value interval in a number of stages (N stages) within a range ($H_1 \leq Hx \leq H_M$) tallying with or including the predicted range of variability of the in-vessel humidity hx ($h_1 \leq hx \leq h_M$), that is $H_1 \leq h_1$, $H_M \geq h_M$. At respective data humidities, $H_1, H_2 \ldots H_M$ are worked out, the output-concentration conversion data $P_1, P_2 \ldots P_M$, from which the respective humidity variable data $Q_1, Q_2 \ldots Q_M$ are obtained. M items of the humidity data $Q_1, Q_2 \ldots Q_M$, each of them comprising N items of output-concentration conversion data $P_1, P_2 \ldots P_M$, make up the temperature-humidity variable data Sx with the temperature and humidity changing within the specific ranges ($T_1 \leq Tx \leq T_M$ and $H_1 \leq Hx \leq H_M$). Those temperature-humidity variable data are identical, in arithmetic operation by the arithmetic unit, to those obtained in the aforesaid procedure. In the following description, the temperature-humidity variable data Sx obtained in the aforementioned procedure will be used.

As an example, FIG. 10 shows part of the temperature-humidity variable data Sx to be stored in the arithmetic unit 74c for sterilization which is carried out in the aforementioned treatment system under the conditions: The in-vessel pressure at atmospheric pressure, an in-vessel humidity of 0.1 to 15 mg/liter, an in-vessel temperature of 20 to 50° C., and an in-vessel concentration of 200 to 2,000 ppm. That is a presentation in a two-way logarithmic graph of the humidity variable data $Q_1, Q_2$ at a data humidity Hx of 0.67 mg/liter, 3.5 mg/liter, each of the humidity variable data $Q_1, Q_2$ comprising output-concentration conversion data $P_1, P_2,$ and $P_3$ at a data temperature of 30° C., 40° C., and 50° C. Measurements were taken under the following conditions and in the following procedures: the experiment vessel was a plastic vessel with a capacity of 136 liters; the aqueous solution of hydrogen peroxide injected into hydrogen peroxide vapor generator 4 was an aqueous hydrogen peroxide solution with a concentration of 31% and a specific gravity of 1.11; the semiconductor gas sensor mounted in the experiment vessel was a Model 812 from Figaro Giken Co., Ltd. of Japan. With the in-vessel pressure at atmospheric pressure and the humidity maintained at 0.67 mg/liter, the temperature in the experiment vessel was changed in three stages: 30° C., 40° C., and 50° C. At each temperature, the concentration of hydrogen peroxide vapor in the experiment vessel was changed in the range between 200 and 2,000 ppm and the output of the semiconductor gas sensor was measured. Also, the temperature in the experiment vessel was changed in three stages of 30° C., 40° C., and 50° C. with the in-vessel pressure fixed at the atmospheric pressure and the humidity maintained at 3.5 mg/liter. At each temperature, the concentration of hydrogen peroxide vapor in the experiment vessel was changed within the range between 200 and 2,000 ppm, with measurements taken of the output of the semiconductor gas sensor. Those measurements were then plotted in a two-way logarithmic graph.

Detection and indication of the in-vessel concentration dx in the third type apparatus 7c are effected according to the third method by the arithmetic unit 74c in which the temperature-humidity variable data Sx obtained as above is stored and the concentration indicator 75 as follows:

The in-vessel humidity hx and the in-vessel temperature tx are first detected by the respective detector 72 and 73. From the temperature-humidity variable data Sx is obtained the temperature variable data $R_E$ worked out at the data humidity $H_E$ corresponding to the detected humidity $h_E$. From the selected temperature variable data $R_E$ is then picked up the output-concentration conversion data $P_F$ obtained at the data temperature $T_F$ corresponding to the detected temperature $t_F$. From this output-concentration conversion data $P_F$ is picked out the data concentration $D_A$ in correlation with the data output $G_A$ corresponding to the sensor output $g_A$, as shown in FIG. 9. The value (the revised value) corresponding to this data concentration $D_A$ is indicated as the concentration of hydrogen peroxide vapor $d_A$ on the concentration indicator 75. Thus, the in-vessel concentration $d_A$ can be shown accurately.

It can happen that even when the in-vessel concentration dx changes, the sensor output $g_A$ will not change if the in-vessel humidity hx and/or the in-vessel temperature tx change. In such cases, too, a correct temperature variable data and an output-concentration conversion data are obtained in accordance with the change in the in-vessel humidity hx and the in-vessel temperature tx. Also, an accurate in-vessel concentration dx is indicated on the concentration indicator 75. If, for example, the in-vessel humidity hx changes from $h_E$ to $h_1$ (or $h_N$) and the in-vessel temperature tx from $t_F$ to data $R_1$ (or $R_N$) these will be detected by the respective detectors 72 and 73, and the temperature variable data $R_1$ (or $R_N$) that were obtained at the data humidity $H_1$ (or $H_N$) corresponding to the detected humidity $h_1$ (or $h_N$) will be selected anew. From this temperature variable data $R_1$ (or $R_N$), furthermore, there will be selected the output-concentration conversion data $R_1$ (or $R_N$) obtained at the data temperature $T_1$ (or $T_M$) corresponding to the detected temperature $t_1$ (or $t_M$). From this output-concentration conversion data $P_1$ (or $P_M$) the data concentration DI (or DN) will be picked out in correlation with the data output GA corresponding to the sensor output $g_A$, as shown in FIG. 9. The value corresponding to this data concentration $D_1$ (or $D_N$) will be displayed on the concentration indicator 75 as the concentration of hydrogen peroxide vapor $d_1$ (or $d_N$). That is, the change of the in-vessel concentration dx from $d_A$ to $d_1$ (or $d_N$) is accurately reflected on the concentration indictor 75.

Conversely, it can happen that even when the in-vessel concentration dx remains unchanged, the sensor output gx changes if the in-vessel humidity hx and/or the in-vessel temperature tx change. In such a case, too, the correct temperature variable data and the correct output-concentration conversion data will be selected in accordance with the changes in-vessel humidity hx and in-vessel temperature tx, with the concentration reading remaining unchanged on the concentration indicator 75. If, for example, the in-vessel humidity hx changes from $h_E$ to $h_1$ (or $h_N$) and the in-vessel temperature tx from $t_F$ to $t_1$ (or $t_M$) with the sensor output gx shifting from $g_A$ to $g_1$ (or $g_M$), there will be picked out a new temperature variable data $R_1$ (or $R_N$) obtained at the data humidity $H_1$ (or $H_N$) corresponding to the detected humidity $h_1$ (or $h_N$). From this temperature variable data $R_1$ (or $R_N$) will furthermore be picked out the output-concentration conversion data $P_1$ (or $P_M$) obtained at the date temperature $T_1$ (or $T_M$) corresponding to the detected temperature $t_1$ (or $t_M$). From this output-concentration conversion data $P_1$ (or $P_M$) the data concentration $D_A$ in correlation with the data output $G_1$ (or $G_M$) corresponding to the sensor output $g_1$ (or $g_M$) is picked out, as shown in FIG. 9. The value corresponding to this data concentration $D_A$ is indicated as the concentration of hydrogen peroxide vapor $d_A$ on the concentration indicator 75. Thus, the reading on the concentration indictor 75 definitely shows that the in-vessel concentration $d_A$ has not changed but remains at $d_A$ while the sensor output gx changes from $g_A$ to $g_1$ (or $g_M$).

This conversion of the sensor output gx into the hydrogen peroxide vapor concentration on the basis of the temperature-humidity, variable data Sx is carried out by comparing the sensor output gx and humidity hx and the detected temperature tx with the variable data Sx stored in the arithmetic unit 74c, a value equal or most approximate to the in-vessel concentration dx is selected. Therefore, a difference between the value and the in-vessel concentration dx can be minimized by working out a further accurate temperature-humidity variable data Sx or by increasing, to the largest possible extent, the number N of the temperature variable data $R_1, R_2 \ldots R_N$ which make up the temperature-humidity variable data Sx and the number M of the output-concentration conversion data $P_1, P_2 \ldots P_M$ forming the respective temperature variable data $R_1, R_2 \ldots R_N$, as well as the number L of detection of the data output and the data concentration at the respective output-concentration conversion data $P_1, P_2 \ldots P_M$.

As illustrated, the third method using the third type apparatus 7c permits direct and real-time accurate detection of the in-vessel concentration dx even under the conditions where the in-vessel humidity hx and/ or the in-vessel temperature tx fluctuate. Thus, the in-vessel concentration dx can be controlled with ease, and sterilization and disinfection of objects 1 to be treated, such as pharmaceutical basic materials, can be carried out efficiently and effectively.

It is to be understood that while specific embodiments of the invention have been shown and described, the invention is not limited thereto and modifications or variations may be made without departing from the spirit and scope of the present invention. In other words, the present invention is applicable not only to the sterilization system as has been described but can be well used in any treatment arrangement for any treatment by supplying hydrogen peroxide vapor into a treatment vessel under the conditions with at least the in-vessel pressure maintained at a constant level irrespective of the treatment conditions and setup. For example, the present invention can also be applied to sterilization and disinfection of installations and furniture in such facilities, for instance, as: medical facilities including sickrooms, consultation rooms, waiting rooms, operation theatres, food processing facilities including kitchens, public facilities including experimental and research laboratories, movie houses, and theaters, transportation means and facilities including warehouses, interior items such as beds, desks, and chairs in buses, trains, ships, and aircraft, with the facilities themselves serving as the treatment vessel.

The in-vessel pressure is not limited to atmospheric pressure as long as it can be kept at a constant level. In case a large area is sterilized or disinfected, (such as a theater serving as the treatment vessel, for example), it is desirable that the hydrogen peroxide gas should be dispersed by a gas diffuser like an axial fan, as necessary. That would spread the hydrogen peroxide gas to every corner of the treatment vessel or such facilities as a theater and make the treatment more effective.

If the humidity detector 72 reacts to the hydrogen peroxide vapor 3 and can not make an accurate detection of the in-vessel humidity in the first type apparatus 7a or the third type apparatus 7c, measurements may be taken of the humidity in the carrier line by installing a humidity detector therein and the line air humidity may be taken as in-vessel humidity.

As is evident from the foregoing description, the method of detecting the concentration of the hydrogen peroxide vapor using a semiconductor gas sensor according to the present invention can directly detect or monitor the concentration of hydrogen peroxide vapor in the treatment vessel with ease and accuracy, thus allowing effective and proper sterilization and disinfection using the hydrogen peroxide vapor. The apparatus for detection of the concentration of the hydrogen peroxide vapor according to the present invention can carry out that method properly.

What is claimed is:

1. A method for deterining by a semiconductor gas sensor the concentration of hydrogen peroxide vapor in a treatment system in which an object to be treated is brought into contact with hydrogen peroxide vapor in a treatment vessel with the pressure kept constant and one of the temperature or the humidity maintained at a constant level, comprising the steps of:

revising the output of said semiconductor gas sensor, in relation to the temperature of the humidity in said treatment vessel, on the basis of data, worked out in advance, representing the correlation between the output of said semiconductor gas sensor and the concentration of hydrogen peroxide vapor in which one of the temperature or humidity is a parameter, and indicting the revised value as concentration of hydrogen peroxide on a concentration indicator.

2. A method for determining by a semiconductor gas sensor the concentration of hydrogen peroxide vapor in a treatment system in which an object to be treated is brought into contact with hydrogen peroxide vapor in a treatment vessel with the pressure maintained at a constant level, comprising the steps of:

revising the output of said semiconductor gas sensor, in relation to the temperature and the humidity in said treatment vessel, on the basis of data, worked out in advance, representing the correlation between the output of said semiconductor gas sensor and the concentration of hydrogen peroxide vapor in which both the temperature and humidity are parameters, and indicating the revised value as concentration of hydrogen peroxide on a concentration indicator.

3. An apparatus for determining the concentration of hydrogen peroxide vapor in a treatment system in which an object to be treated is brought into contact with hydrogen peroxide vapor in a treatment vessel with the pressure kept constant and one of the temperature or the humidity maintained at a constant level, comprising:

- a gas semiconductor sensor for determining the concentration of hydrogen peroxide vapor in the treatment vessel,
- a detector for determining the temperature or the humidity in the treatment vessel,
- an arithmetic unit for revising the output of said semiconductor gas sensor, in relation to the temperature or the humidity detected by the detectors in said treatment vessel, on the basis of data, worked out in advance, representing the correlation between the output of said semiconductor gas sensor and the concentration of hydrogen peroxide vapor in which one of the temperature or humidity is a parameter, and
- an indicator for indicating the revised value obtained by the arithmetic unit as concentration of hydrogen peroxide.

4. An apparatus for determining the concentration of hydrogen peroxide vapor in a treatment system in which an object to be treated is brought into contact with hydrogen peroxide vapor in a treatment vessel with the pressure maintained at a constant level, comprising:

- a gas semiconductor sensor for determining the concentration of hydrogen peroxide vapor in the treatment vessel,
- detectors for determining the temperature and the humidity in the treatment vessel,
- an arithmetic unit for revising the output of said semiconductor gas sensor, in relation to the temperature and the humidity detected by the detectors in said treatment vessel, on the basis of data, worked out in advance, representing the correlation between the output of said semiconductor gas sensor and the concentration of hydrogen peroxide vapor in which both the temperature and the humidity are parameters, and
- an indicator for indicating the revised value as concentration of hydrogen peroxide on a concentration indicator.

* * * * *